United States Patent
Stevenson et al.

(10) Patent No.: US 7,797,048 B2
(45) Date of Patent: Sep. 14, 2010

(54) FEEDTHROUGH FILTER TERMINAL ASSEMBLIES WITH BREATHABLE COMPONENTS TO FACILITATE LEAK TESTING

(75) Inventors: Robert A. Stevenson, Canyon Country, CA (US); Christine A. Frysz, Orchard Park, NY (US); Jennifer L. Stevenson, Canyon Country, CA (US); Haytham Hussein, Woodstock, MD (US)

(73) Assignee: Greatbatch Ltd., Clarence, NY (US)

( * ) Notice: Subject to any disclaimer, the term of this patent is extended or adjusted under 35 U.S.C. 154(b) by 706 days.

(21) Appl. No.: 11/689,782

(22) Filed: Mar. 22, 2007

(65) Prior Publication Data

US 2008/0294220 A1    Nov. 27, 2008

Related U.S. Application Data

(60) Provisional application No. 60/767,483, filed on Apr. 3, 2006.

(51) Int. Cl.
*A61N 1/375*    (2006.01)

(52) U.S. Cl. ............................................ 607/37
(58) Field of Classification Search .................... 607/37
See application file for complete search history.

(56) References Cited

U.S. PATENT DOCUMENTS

| | | | |
|---|---|---|---|
| 4,259,402 A * | 3/1981 | Cobbs et al. | ............. 428/317.5 |
| 4,424,551 A | 1/1984 | Stevenson et al. | |
| 5,333,095 A | 7/1994 | Stevenson et al. | |
| 5,751,539 A | 5/1998 | Stevenson et al. | |
| 5,905,627 A | 5/1999 | Brendel et al. | |
| 5,973,906 A | 10/1999 | Stevenson et al. | |
| 6,008,980 A | 12/1999 | Stevenson et al. | |
| 6,551,608 B2 * | 4/2003 | Yao | ............................ 424/409 |
| 6,566,978 B2 | 5/2003 | Stevenson et al. | |
| 6,765,779 B2 * | 7/2004 | Stevenson et al. | ........... 361/302 |
| 6,979,356 B1 * | 12/2005 | Carson | ...................... 29/25.03 |

(Continued)

OTHER PUBLICATIONS

Antonio Garcia Loera, et al., Porous Epoxy Thermosets Obtained by a Polymerization-Induced Phase Separation Process of a Degradable Thermoplastic Polymer, Macromolecules, 2002, 35, 6291-6297.

(Continued)

*Primary Examiner*—Carl H Layno
*Assistant Examiner*—Jeremiah T Kimball
(74) *Attorney, Agent, or Firm*—Kelly Lowry & Kelley, LLP (57) ABSTRACT

A feedthrough terminal assembly for an active implantable medical device (AIMD) includes a conductive terminal pin or lead wire which extends through a conductive ground plane of the AIMD in non-conductive relation. A feedthrough capacitor associated with the terminal pin or lead wire has first and second sets of electrode plates coupled, respectively, to the conductive pin or lead wire and to the ground plane. A breathable electromechanical connection material conductively couples the capacitor's electrode plates to respective components of the AIMD, which allows helium gas to pass freely therethrough during a standard pressurized or vacuum pull helium leak detection test. A breathable washer may be disposed between an alumina insulator and a surface of the capacitor. An additional further breathable coating or conformal coating may be placed over a surface of the feedthrough capacitor disposed toward the interior of the AIMD.

51 Claims, 7 Drawing Sheets

U.S. PATENT DOCUMENTS

| | | |
|---|---|---|
| 6,989,433 B2 | 1/2006 | Wong et al. |
| 2002/0034827 A1* | 3/2002 | Singh et al. ................ 436/177 |
| 2005/0048121 A1* | 3/2005 | East et al. .................. 424/486 |
| 2006/0023397 A1 | 2/2006 | Brendel |

OTHER PUBLICATIONS

Qipeng Guo, et al., Phase Separation, Porous Structure, and Cure Kinetics in Aliphatic Epoxy Resin Containing Hyperbranched Polyester, Journal of Polymer Science: Part B: Polymer Phsics 2006, vol. 44, 889-899.

* cited by examiner

BODY FLUID SIDE

BODY FLUID SIDE

BODY FLUID SIDE

FEEDTHROUGH FILTER TERMINAL ASSEMBLIES WITH BREATHABLE COMPONENTS TO FACILITATE LEAK TESTING

BACKGROUND OF THE INVENTION

This invention relates generally to feedthrough terminal assemblies, particularly of the type used in implantable medical devices such as cardiac pacemakers, cardioverter defibrillators and the like, to decouple and shield internal electronic components of the medical device from undesirable electromagnetic interference (EMI) signals. More specifically, this invention relates to an improved feedthrough capacitor filtered terminal assembly of the type incorporating a hermetic seal to prevent passage or leakage of fluids through the terminal assembly, wherein breathable components are provided to accommodate and facilitate post manufacture and pre-usage testing of the hermetic seal.

Feedthrough terminal pin assemblies are generally well known in the art for use in connecting electrical signals through the housing or case of an electronic instrument. For example, in active implantable medical devices such as cardiac pacemakers, defibrillators and the like, the terminal pin assembly comprises one or more conductive terminal pins supported by an insulator structure for feedthrough passage of electrical signals from the exterior to the interior of the medical device. Many different insulator structures and related mounting methods are known for use in medical devices wherein the insulator structure provides a hermetic seal to prevent entry of patient body fluids into the medical device housing, where such body fluids could otherwise interfere with the operation of and/or cause damage to internal electronic components of the medical device.

In the past, two primary technologies have been employed to manufacture the hermetic seal. One technique involves the use of a ceramic insulator, typically alumina, which is sputtered to accept brazing material. This alumina insulator is brazed to the terminal pin or pins, and also to an outer metal ferrule of titanium or the like. The alumina insulator supports the terminal pin or pins in insulated spaced relation from the ferrule which is adapted for suitable mounting within an access opening formed in the housing of the medical device. In an alternative technique, the hermetic seal comprises a glass or glass-ceramic based seal forming a compression or matched glass seal for supporting the terminal pin or pins within an outer metal ferrule.

The feedthrough terminal pins are typically connected to one or more lead wires which, in the example of a cardiac pacemaker, sense signals from the patient's heart and also couple electronic pacing pulses from the medical device to the patient's heart. Unfortunately, these lead wires can act as an antenna to collect stray EMI signals for transmission via the terminal pins into the interior of the medical device. Such unwanted EMI signals can disrupt proper operation of the medical device, resulting in malfunction or failure. For example, it has been documented that stray EMI signals emanating from cellular telephones can inhibit pacemaker operation, resulting in asynchronous pacing, tracking and missed beats. To address this problem, hermetically sealed feedthrough filter terminal assemblies have been designed to include a filter capacitor for decoupling EMI signals in a manner preventing such unwanted signals from entering the housing of the implantable medical device. See, for example, U.S. Pat. Nos. 4,424,551; 5,333,095; 5,751,539; 5,905,627; 5,973,906; 6,008,980; and 6,566,978.

While feedthrough capacitor filter terminal assemblies have provided a significant advancement in the art, one potential area of concern is that the filter capacitor is often incorporated into the terminal pin assembly in a way that can mask a defective hermetic seal. More particularly, detection of a defective braze or a defective glass-based seal structure, which would permit undesirable leakage of patient body fluids when mounted on a medical device and implanted into a patient, can be obstructed by the mounting of the filter capacitor and its associated electromechanical connections. For example, with reference to the feedthrough filter capacitor shown in U.S. Pat. No. 4,424,551, a ceramic filter capacitor is bonded to a glass seal and then embedded in epoxy material. Typical post-manufacture leak testing is performed by mounting the feedthrough terminal assembly in a test fixture, and then subjecting one side of the feedthrough terminal assembly to a selected pressurized gas, such as helium. While the bulk permeability of the epoxy material is such that helium under pressure can penetrate therethrough in the presence of a defective hermetic seal, the duration of this pressure test (typically only a few seconds) is often insufficient to permit such penetration. Accordingly, the epoxy material can mask a defective hermetic seal. The thus-tested feedthrough terminal assembly can then mistakenly be incorporated into a medical device and implanted into a patient, wherein slow leakage of patient body fluids through the feedthrough assembly can cause the medical device to malfunction or fail.

Figure 1:
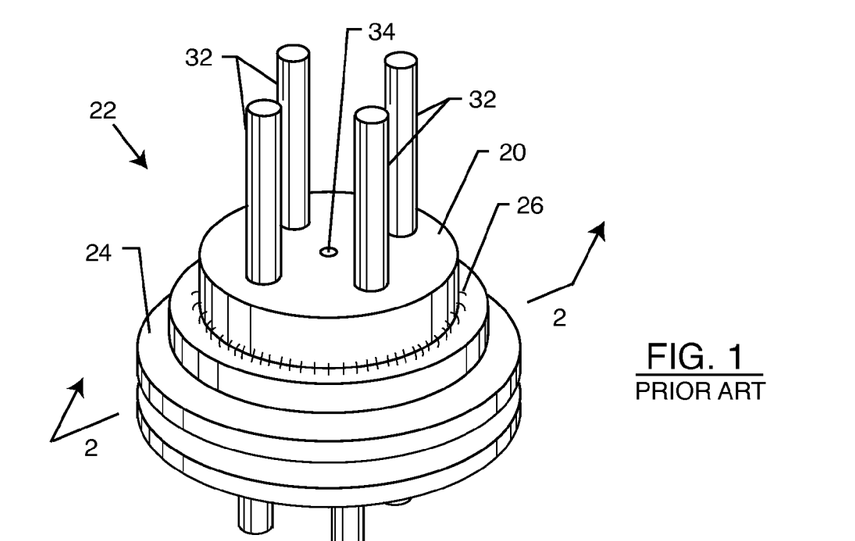
FIG. 1 is an isometric view of a prior art quadpolar feedthrough capacitor mounted to a quadpolar hermetic terminal assembly.
Figure 2:
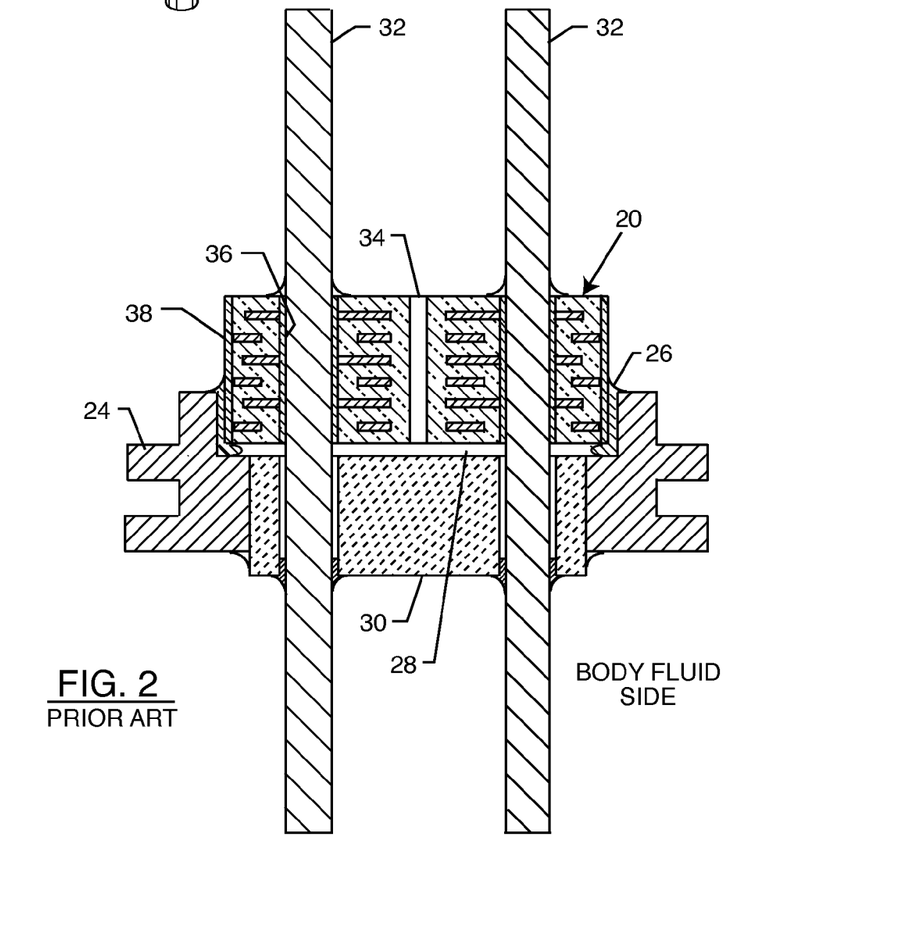
FIG. 2 is a cross-sectional view taken along line 2-2 of FIG. 1.

One method to resolve this issue is depicted in FIGS. 1 and 2, which are similar to FIGS. 1 and 2 of U.S. Pat. No. 6,566,978, the contents of which are incorporated herein. These figures disclose a quadpolar feedthrough capacitor 20 mounted on a quadpolar feedthrough terminal assembly 22 and affixed to the ferrule 24 by means of non-porous electromechanical connection 26. The electromechanical connection material 26 around the entire perimeter of the capacitor 20 has bulk permeability insufficient to permit passage of helium gas (or other testing medium) during a leak detection test of standard duration. In order to facilitate leak detection testing in this prior art device, a gap 28 is formed between the ceramic capacitor 20 and the alumina hermetic seal insulator 30. The purpose of this gap 28 is to allow for ready passage of leak detection gases from the hermetic terminal areas or along lead wire 32 through the insulator 30 to flow to a leak detection vent hole 34. However, providing such a gap 28 between the ceramic capacitor 20 and the insulator 30 surface can result in the tendency to trap contaminants, cleaning solvents or the like into this enclosed space. Conductive polyimides or conductive epoxies or solders are typically used to form the electrical connection between the lead wire 32 and the inside diameter metallization 36 of the ceramic capacitor 20. Conductive polyimides or epoxies are also typically used to form the connection between the capacitor 20 outside diameter metallization 38 and the ferrule 24.

After curing, these conductive polyimide or epoxy materials are typically cleaned using a grit blasting system with sodium bicarbonate as the blasting medium. Sodium bicarbonate, otherwise known as baking soda, is highly soluble in water. Accordingly, de-ionized water rinses are used to ensure that no baking soda is left on the part as the sodium bicarbonate dissolves readily into the water cleaning solvent. After drying out, trace elements of the sodium bicarbonate can be left inside any cavity or air gap, for example, the gap 28 formed between the ceramic capacitor 20 and the alumina insulator 30. The sodium bicarbonate residue is hygroscopic. That is, it will tend to absorb moisture from the surrounding air which can degrade the electrical insulation properties of the quadpolar feedthrough terminal assembly 22.

For medical implant applications, it is typical that the insulation resistance requirement be 10 Gigaohms or even higher. In order to consistently achieve an insulation resistance greater than 10 Gigaohms, it is essential that all surfaces be extremely clean. Accordingly, any trace element of sodium bicarbonate or other contaminant left behind leads to rejection of the devices due to lowering of the insulation resistance below 10 Gigaohms.

Another issue associated with the gap 28 between the ceramic capacitor 20 and the insulator 30 is associated with the high voltage requirements of an implantable cardioverter defibrillator (ICD). Even low voltage devices like pacemakers are sometimes subjected to high voltage pulses. This is typical during an external defibrillation event. There has been a proliferation of automatic external defibrillators (AEDs) in the marketplace. One can now find AEDs in airplanes, hotels, sporting places and many other public venues. Accordingly, pacemaker wearers are being subjected to an ever-increasing number of high voltage shocks in the patient environment. One can see that the gap 28 is an area where electric field enhancement can occur. That is, when a high voltage is applied to the lead wires 32, there could be a tendency for a high electric field stress to occur in the air gap 28. These high electric field stresses can lead to ionization of the air gap 28, a resulting plasma, and a catastrophic high voltage breakdown of the assembly 20. This so called avalanche breakdown would cause an implantable medical device to not function, which would of course be life threatening for a pacemaker or defibrillator dependent patient.

Figure 3:
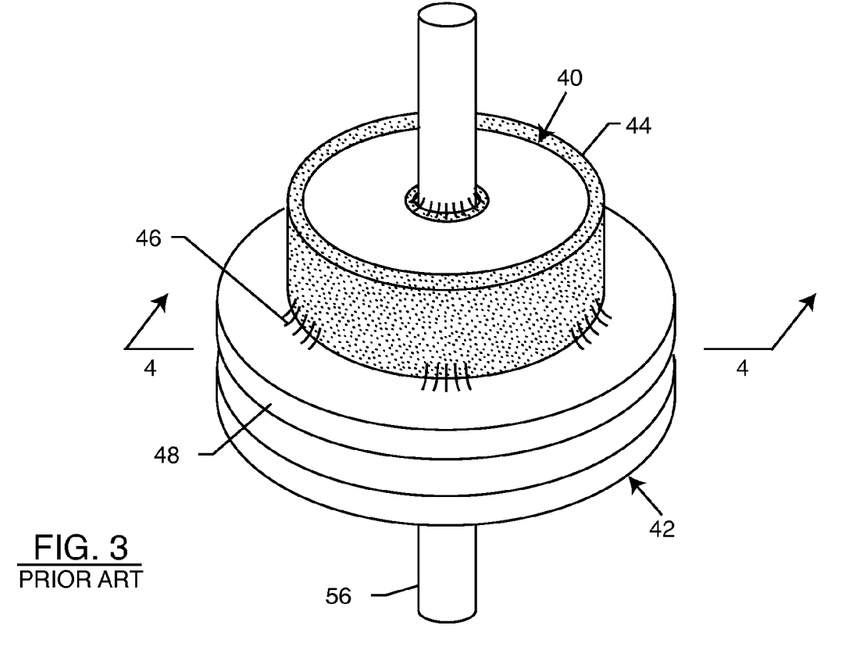
FIG. 3 is an isometric view of a prior art unipolar feedthrough capacitor mounted to a unipolar hermetic terminal assembly.
Figure 4:
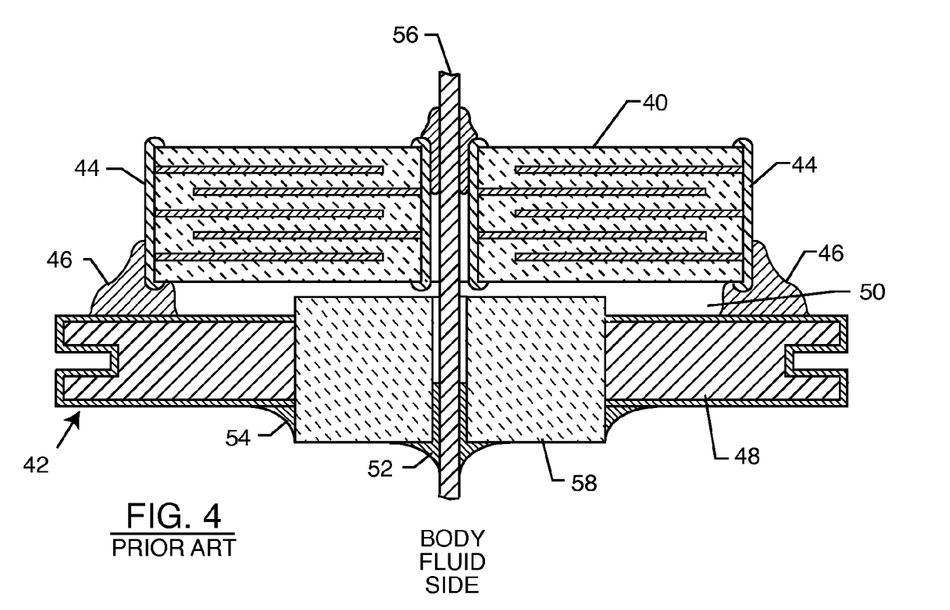
FIG. 4 is a cross-sectional view taken along line 4-4 of FIG. 3.

Another method to resolve the issue of leak detection testing is depicted in FIGS. 3 and 4, which are similar to FIGS. 5 and 6 of U.S. Pat. No. 6,765,779, the contents of which are incorporated herein. FIGS. 3 and 4 disclose a unipolar feedthrough capacitor 40 mounted on a hermetic terminal assembly 42. The feedthrough capacitor 40 incorporates outer diameter metallization 44. An electrical attachment 46 is made from the capacitor outside diameter metallization 44 to the ferrule 48. This connection 46 is typically formed with a high temperature thermosetting conductive polymer such as a conductive polyimide. There are gaps left around the circumference of connection material 46 to provide helium leak detection pathways. This is generally described in U.S. Pat. No. 6,765,779 in column 2, lines 24 through 67 and in column 3 lines 1 through 33. There is also an axial gap 50 formed between the feedthrough capacitor 40 and the surface of the hermetic terminal 42. The purpose of this axial gap 50 is so that if there was a defective gold braze 52, 54, helium atoms could readily penetrate the annular space between the lead wire 56 and the inside diameter of the insulator 58. Accordingly, said helium atoms could then pass readily through the axial gap 50 and out through the spaces left in the circumferential conductive polyimide attachment material 46. As previously mentioned, leaving an axial gap 50 can trap contaminants between the capacitor 40 and the insulator 58 of the terminal assembly 42 and also has the tendency to enhance (squeeze or compress) electric fields during the application of a high voltage to the device.

Accordingly, there is a need for an EMI filtered hermetic feedthrough terminal assembly suitable for human implant that will avoid the issues associated with an air gap and/or leak detection pathways, but at the same time provide for a helium leak detection path. The present invention fulfills this need by providing an improved feedthrough terminal assembly suitable for use in an implantable medical device or the like, wherein the feedthrough assembly includes breathable electromechanical connections, breathable washers and breathable coatings and conformal coatings for accommodating and facilitating post-manufacture hermetic seal leak testing.

SUMMARY OF THE INVENTION

In accordance with the invention, an improved feedthrough terminal assembly for use in an active implantable medical device (AIMD) is provided. The AIMD may comprise a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a nerve stimulator, a bone growth stimulator, a gastric pacemaker, a prosthetic device, or the like.

The medical device comprises a conductive terminal pin or lead wire extending through a conductive ground plane of the AIMD in non-conductive relation. The ground plane may comprise a ferrule or a housing for the AIMD. A feedthrough capacitor is associated with the conductive terminal pin or lead wire, and has first and second sets of electrode plates. Means are provided for conductively coupling the first and second electrode plates to the terminal pin or lead wire. Means are also provided for conductively coupling the second set of electrode plates to the ground plane.

In one embodiment, at least one of the conductive coupling means comprises a breathable electromechanical connection material which allows a leak detection gas to pass therethrough during a standard pressurized or vacuum pull leak detection test.

For the present invention, breathable means that the component in question has sufficient bulk permeability so as to pass a leak detection gas therethrough, while preventing liquids and solid materials to pass therethrough. More particularly, such components are considered to be breathable if they freely pass helium gas during a standard pressurized or vacuum pull helium leak detection test, which typically is performed in less than one minute.

The assembly may include a hermetic insulator adjacent to a face of the capacitor and disposed between the terminal pin or lead wire and the conductive ground plane. Typically, a washer is disposed between the hermetic insulator and the capacitor.

In an embodiment of the present invention, the washer comprises a breathable washer which allows a leak detection gas to pass therethrough during a standard pressurized or vacuum pull leak detection test. The washer may include an adhesive layer comprising a breathable material which allows a leak detection gas to pass therethrough during a standard pressurized or vacuum pull leak detection test.

A coating or conformal coating may be disposed over the capacitor on a surface disposed toward the inside of the AIMD. The coating or conformal coating may comprise a breathable material which allows a leak detection gas to pass therethrough during a standard pressurized or vacuum pull leak detection test.

The present invention also resides in a process for assembling a feedthrough terminal assembly for an active implantable medical device (AIMD), comprising the steps of providing a feedthrough capacitor having first and second sets of electrode plates. The first set of electrode plates are conductively coupled to a conductive terminal pin or lead wire extending through the feedthrough capacitor. The second set of electrode plates are conductively coupled to a ground plane for the AIMD, which may comprise a ferrule or a housing for the AIMD.

In one embodiment, during at least one of the coupling steps, the associated components are electromechanically joined with a breathable material which allows a leak detection gas to pass through the coupling during a standard pressurized or vacuum pull leak detection test. Alternatively, or in addition, a washer of breathable material may be provided adjacent to a surface of the capacitor. Typically, the washer is disposed between the capacitor and a hermetic insulator. Alternatively, or in addition, a surface of the capacitor may be coated or conformally coated with a breathable material.

The washer may comprise a compressible gas permeable gasket or membrane. The washer may also comprise a fiber washer, a double corrugated washer, a perforated washer, or a post casting stretched membrane washer. The material is treated to create sufficient permeability to allow the leak detection gas to pass therethrough, while excluding movement of liquids, dissolved solids and/or solid contaminants therethrough, thus making it breathable. For example, the treating process may comprise the steps of incorporating into a molten thermoplastic a surfactant in a sufficient gas-stabilizing amount. The dispersion is pressurized to form a hot solution of the gas in the molten thermoplastic. The hot solution is dispensed under lower pressure, whereby the gas is released from the solution to form a hot foamed material. The hot foam is compressed between two substrates, such as the capacitor and the insulator, to force the gas from the foam.

Another treatment process to create the desired permeability includes the steps of polymerization-induced phase separation of a thermoplastic at a moderate temperature, followed by a high temperature treatment to cause oxidative thermal degradation of the thermoplastic. Typically, in such a treatment process, the material comprises an epoxy-amine cross-linked matrix having a diamine monomer and a polyvinyl, polymethyl, and/or polyether additive.

Yet another treatment process includes the steps of selectively removing the hyperbranched polymer phase of a cured epoxy/hyperbranched polymer blend using a solvent.

Still another treatment process includes the steps of adding porous fillers to the material. The porous fillers are selected from the group consisting of porous insulative spheres, porous insulative nanotubes, open cell microspheres, microtublets, talc, porous filaments, nanofoams, and porous fibers.

Adhesive material may be selectively applied to surfaces of the washer without compromising permeability and leak testability of the surrounding breathable medium. Such adhesive material may be desirable for adhering the washer to an adjacent structure, preventing undesirable flow of a conductive polyimide, or to prevent arcing or high-voltage flashover.

Additional objects and advantages of the invention will be set forth in part in the drawings which follow, and in part will be obvious from the description or may be learned by practice of the invention. It is to be understood that both the foregoing general description and the following drawings are exemplary and explanatory only and are not restrictive of the invention as claimed.

BRIEF DESCRIPTION OF THE DRAWINGS

The accompanying drawings illustrate the invention. In such drawings.

DETAILED DESCRIPTION OF THE PREFERRED EMBODIMENTS

An improved feedthrough capacitor filter terminal assembly is provided for use in active implantable medical devices (AIMDs) and the like, such as in a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a nerve stimulator, a bone growth stimulator, a gastric pacemaker, or a prosthetic device.

Figures 5, 6, 7:
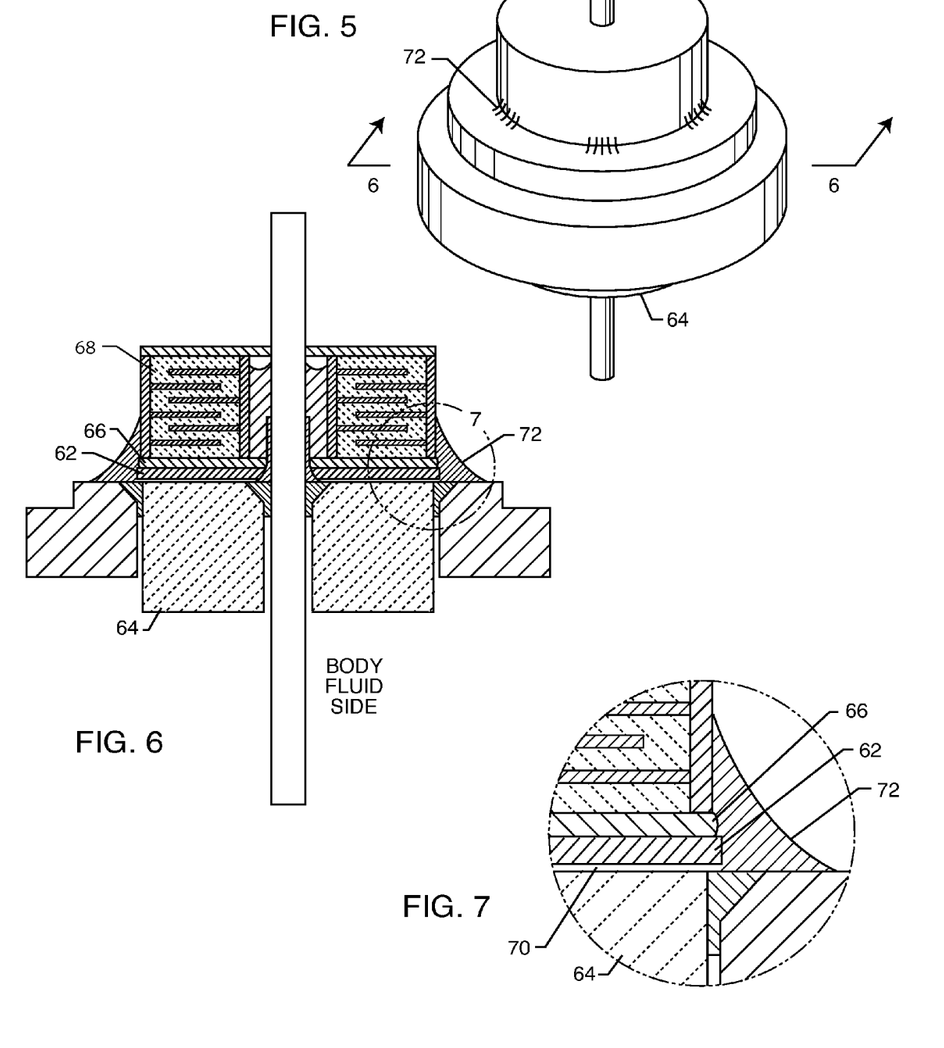
FIG. 5 is an isometric view of a unipolar feedthrough capacitor mounted to a unipolar hermetic terminal.
FIG. 6 is a cross-sectional view taken along line 6-6 of FIG. 5.
FIG. 7 is an enlarged view taken of the area indicated by the number 7 in FIG. 6.

A prior method of resolving the issues of leak testing is depicted in FIGS. 5, 6 and 7, taken from co-pending U.S. patent application Ser. No. 11/161,198, the contents of which are incorporated herein. These figures depict a unipolar feedthrough terminal assembly 60 similar to that shown in FIGS. 3 and 4. However, a non-conductive and non-adhesive washer 62 has been added and is pressed firmly against the top surface of the alumina insulator 64, and one or more adhesive layers 66 have been placed on top of the washer 62. The capacitor 68 is then seated into place on top of the adhesive layers 66. The top surface of the adhesive layer 66 laminates to the bottom of the capacitor 68 and the bottom surface of the adhesive layer 66 laminates to the top of the washer 62. The bottom surface of the washer 62 is not laminated to the top surface of the insulator 64. This construction leaves a laminar delamination gap 70 that is a very thin gap which is sufficient to readily allow helium atoms to pass during a helium leak detection test without permitting the passage of larger molecules or compounds, i.e., water, sodium bicarbonate, etc. Electromechanical connection material 72 is spaced around the perimeter of the capacitor 68 similar to the gaps left around the circumference of connection material 46 in FIGS. 3 and 4. These gaps provide helium leak detection pathways to permit helium (or similar) atoms to pass during a leak detection test. However, the presence of the thin air gap 70 can still lead to high voltage field enhancement and arcing.

In accordance with the present invention, and as shown in FIGS. 8-18, there are three categories of breathable materials utilized in feedthrough terminal assemblies embodying the present invention:

1) The first category is breathable electromechanical connections. These electrical-mechanical connections, in general, connect between the capacitor active electrode plate set and one or more lead wires. The electromechanical connections can also be used to connect between the capacitor ground electrode plate set and the overall electromagnetic ground plane shield and/or ferrule of the hermetic terminal.

2) The second category is breathable washers. These washers may be preformed or dispensed. They can be thermosetting, B-staged, compressible or rigid with adhesive coatings. Such breathable washers lay intermediate between the ceramic feedthrough capacitor and its underlying mounting surface. In general, for an EMI filtered hermetic terminal for an AIMD, these washers are intermediate between the ceramic capacitor and the alumina or glass hermetic seal.

3) The third category is breathable coatings and breathable conformal coatings that are placed on top of the ceramic capacitor (the surface disposed toward the inside of the AIMD housing). These breathable coatings provide mechanical strength, improve the cosmetic appearance and also improve the high voltage characteristics of the capacitor.

For the present invention, breathable means "free to pass detection gas, such as helium, during a standard pressurized or vacuum pull leak detection test", which typically is performed in less than one minute.

Breathable electromechanical connections mainly consist of a thermosetting conductive material, such as a conductive epoxy, conductive polyimide, conductive silicone or the like. In general, these dispersible materials are conductive because they have been loaded with metallic flakes or spheres, such as silver or the like. In order to make these electromechanical connection materials porous in accordance with the present invention, porous fillers are added. This includes the entire category of breathable fillers, examples of which include porous carbon spheres, carbon nanotubes, open cell microspheres, microtublets, talc, porous filaments, carbon nanofoams, porous fibers or the like. For example, carbon nanofoams are electrically conductive, have high capacitance, and have continuous porosity and nanometer-scale dimensions.

Alternatively, pores can be formed in the thermosetting material using a variety of methods. In one such method, pores with either submicrometer-sized closed-cell structure or a bicontinuous percolating structure ("canallike") can be formed in an electrically-conductive epoxy-amine cross-linked matrix utilizing the polymer additives poly-(vinyl methyl ether) (PVME) and a diamine monomer (such as polyoxyproylene diamine or polyoxyprolene triamine), and a two-step temperature cure: a polymerization-induced phase separation at a moderate temperature (100-120° C.) of a thermoplastic, . . . PVME . . . , in an epoxy-amine matrix followed by a high-temperature treatment (above 200° C.), as disclosed in Loera et al. *Porous Epoxy Thermosets Obtained by a Polymerization-Induced Phase Separation Process of a Degradable Thermoplastic Polymer*. Macromolecules 2002, 35, 6291-6297, the contents of which are incorporated herein by reference. The two-step temperature cure will not only allow the formation of pores within the epoxy, but also provides an additional safeguard to prevent sodium bicarbonate contamination, in that cleaning can be performed after bonding to the ceramic at the moderate temperature (before the pores are formed), after which the material can be treated at the higher temperature, allowing pore formation.

A different technique for forming porous epoxy thermoset, in which a solvent (THF) is used to selectively remove the hyperbranched polymer phase of a cured electrically-conductive epoxy/hyperbranched polymer blend, is also known, as disclosed in Guo et al. *Phase Separation, Porous Structure, and Cure Kinetics in Aliphatic Epoxy Resin Containing Hyperbranched Polyester*. Journal of Polymer Science: Part B: Polymer Physics 2006, Vol. 44, 889-899, the contents of which are incorporated herein by reference.

Breathable washers include materials that can be dispensed, can be set in place as a solid object, or compressed. Certain breathable washer materials include the same group as previously described for electromechanical connections except that in this case they are insulative (not filled with silver spheres or flake). This would include thermosetting epoxies, polyimides, plastics, silicones and the like. To make them breathable, they are filled with one or more porous fillers, including breathable fillers, porous insulative spheres, porous insulative nanotubes, open cell microspheres, microtublets, talc, porous filaments, porous fibers, silica powder, silica aerogel, or the like.

Alternatively, pores can be formed in the thermosetting material using a variety of methods. In one such method, pores with either submicrometer-sized closed-cell structure or a bicontinuous percolating structure ("canallike") can be formed in an epoxy-amine cross-linked matrix utilizing the polymer additives poly-(vinyl methyl ether) (PVME) and a diamine monomer (such as polyoxyproylene diamine or polyoxyprolene triamine), and a two-step temperature cure: a polymerization-induced phase separation at a moderate temperature (100-120° C.) of a thermoplastic, . . . PVME . . . , in an epoxy-amine matrix followed by a high-temperature treatment (above 200° C.) (Loera et al. Macromolecules 2002, 35, 6291-6297). The two-step temperature cure will not only allow the formation of pores within the epoxy, but also provides an additional safeguard to prevent sodium bicarbonate contamination, in that cleaning can be performed after bonding to the ceramic at the moderate temperature (before the pores are formed), after which the material can be treated at the higher temperature, allowing pore formation. A different technique for forming porous epoxy thermoset, in which a solvent (THF) is used to selectively remove the hyperbranched polymer phase of a cured epoxy/hyperbranched polymer blend, is also known (Guo et al. Journal of Polymer Science: Part B: Polymer Physics 2006, Vol. 44, 889-899).

Additionally, foamed hot-melt adhesives, formed by first stabilizing a dispersion of gas bubbles in a molten thermoplastic by incorporating in the molten thermoplastic a surfactant in a sufficient gas-stabilizing amount, subsequently pressurizing said dispersion to form a hot solution of the gas in the molten thermoplastic, dispensing said hot solution under lower pressure whereby said gas is released from said solution to form a hot foamed material, and compressing the hot foam between two substrates to force the gas from the foam and to form a bond between the substrates, can be used, as disclosed in U.S. Pat. No. 4,259,402, the contents of which are incorporated herein by reference.

There is another group of washers that includes the group of compressible gas permeable gaskets and membranes. For example, a thick layer of Gore-Tex (a gas permeable membrane) could be compressed between the ceramic capacitor and an alumina ceramic insulator. This would require that the capacitor be seated under pressure while the electromechanical connections are made between the capacitor outer diameter and the ferrule and/or the capacitor inner diameter hole(s) and lead wire(s). This would keep the capacitor firmly seated against the compressible porous membrane in a way that water and other contaminants are precluded from entering between the surfaces of the ceramic capacitor and the compressed membrane. However, in this case, the membrane would be semi-permeable or breathable. This would allow helium to freely pass while at the same time firmly seating the ceramic capacitor. Firmly seating the ceramic capacitor against these compressible surfaces eliminates small air gaps which cause high voltage stress risers in implantable defibrillator applications or in the case where external defibrillation is applied to a patient.

Breathable washers also include the group of breathable thermoplastics and breathable membranes. These breathable thermoplastics and breathable membranes can be coated with very thin layers of thermosetting adhesives. This allows these washers to be bonded both to the ceramic feedthrough capacitor and to the insulator bonding surfaces thereby preventing the formation of thin air gaps as mentioned above. As long as the thermosetting adhesive layer is kept very thin, this will still allow the leak detection gas, typically helium atoms, to pass quickly through.

Another category of breathable washers includes structurally formed washers, including hot or heat-seal installation and fabrication methods. This includes fiber washers, double corrugated washers, perforated washers and post casting stretched membranes which create mircoperforations.

In accordance with the invention, breathable coatings and breathable conformal coatings are generally used to coat the top surface of the capacitor. This is the surface that is pointed towards the inside of the AMID. The purpose of these coatings or conformal coatings is three fold: that is, to provide mechanical protection against handling for solvent cleaning during manufacturing of the AIMD, to provide a nice cosmetic finished appearance, and to improve the high voltage characteristics of the ceramic capacitor. In general, it is preferred that these coatings be very thin because they are mismatched in thermal coefficient of expansion with the underlying ceramic capacitor. A thin layer does not induce microfractures in or pull away from the relatively brittle ceramic capacitor materials. Conformal coatings are highly desirable in high voltage applications. This is because of the relatively high dielectric constant or permeability of the ceramic capacitor itself. The ceramic capacitor, for example, can have a dielectric constant (k) in excess of 2500. Air only has a dielectric constant of 1. When high voltage fields make a transition from such a high k material to a relatively low k material, field enhancements occur which can lead to arc-overs, surface cracks or even catastrophic high voltage avalanche breakdown of the ceramic capacitor. By adding a material of intermediate dielectric constant, such as an epoxy, polyimide, plastic or silicone material, the high voltage field is relaxed thereby creating much less tendency for arcing or high voltage breakdown to occur across the capacitor surface. In accordance with the present invention, these coatings and conformal coatings are breathable.

In order to make them breathable such that helium can pass through readily, they are in general loaded with a breathable filler, including the group of porous insulative spheres, carbon nanotubes, shortcut aligned fibers or whiskers that are porous, open cell microspheres, microtublets, talc, porous filaments, porous fibers, silica powder, silica aerogel, or the like.

Alternatively, pores can be formed in the thermosetting material using a variety of methods. In one such method, pores with either submicrometer-sized closed-cell structure or a bicontinuous percolating structure ("canallike") can be formed in an epoxy-amine cross-linked matrix utilizing the polymer additives poly-(vinyl methyl ether) (PVME) and a diamine monomer (such as polyoxyproylene diamine or polyoxyprolene triamine), and a two-step temperature cure: a polymerization-induced phase separation at a moderate temperature (100-120° C.) of a thermoplastic, . . . PVME . . . , in an epoxy-amine matrix followed by a high-temperature treatment (above 200° C.) (Loera et al. Macromolecules 2002, 35, 6291-6297). The two-step temperature cure will not only allow the formation of pores within the epoxy, but also provides an additional safeguard to prevent sodium bicarbonate contamination, in that cleaning can be performed after bonding to the ceramic at the moderate temperature (before the pores are formed), after which the material can be treated at the higher temperature, allowing pore formation.

A different technique for forming porous epoxy thermoset, in which a solvent (THF) is used to selectively remove the hyperbranched polymer phase of a cured epoxy/hyperbranched polymer blend, is also known (Guo et al., Journal of Polymer Science Part B: Polymer Physics 2006, Vol. 44, 889-899).

Also, breathable conformal coatings for the purpose of aiding hermeticity testing can be formed by a composition/formulation containing a rubber, siloxane or urethane oligomer modified epoxy and an organic hardener, and optionally an organic diluent and a curing catalyst or a composition/formulation containing a silicone elastomer or gel and a metal chelate catalyst, and optionally a silica filler, a diluent and an adhesion promoter or coupling agent, as disclosed in U.S. Pat. No. 6,989,433, the contents of which are incorporated herein by reference.

Figures 8, 9, 10:
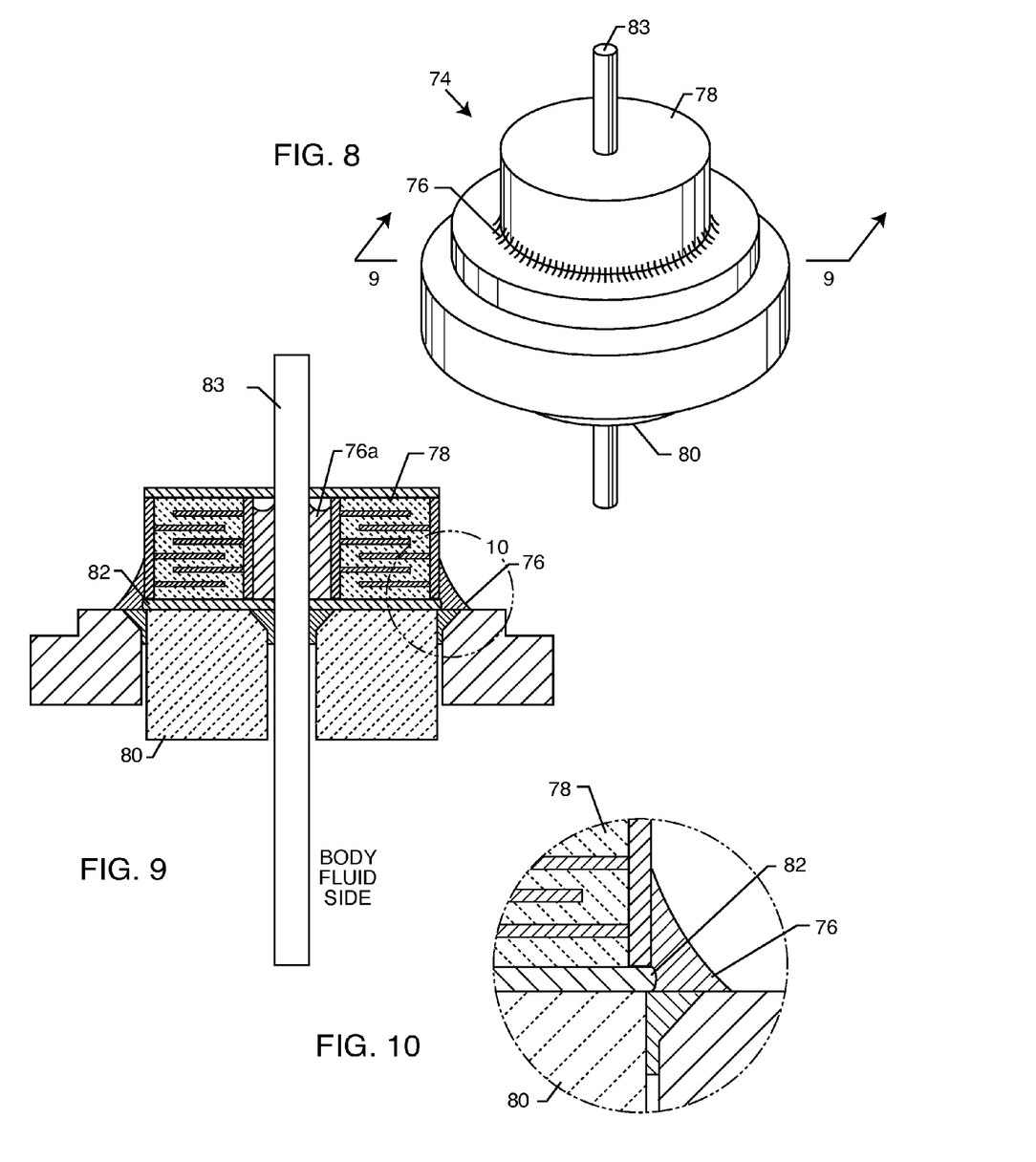
FIG. 8 is an isometric view of a unipolar feedthrough capacitor mounted to a unipolar hermetic terminal assembly embodying the present invention.
FIG. 9 is a cross-sectional view taken along line 9-9 of FIG. 8.
FIG. 10 is an enlarged view taken of the area indicated by the number 10 in FIG. 9.

With specific reference to a first preferred embodiment illustrated in FIGS. 8-10, a unipolar feedthrough terminal assembly 74 is shown which is similar to the terminal assemblies 22, 42 and 60 described above. However, there are a number of important improvements. Where electrical connection material 46 and 72 had previously been spaced with discontinuous gaps around the perimeter of the capacitor 44 and 68, it can now be a continuous uninterrupted ring of breathable conductive electromechanical connection material 76. Additionally, a breathable washer 82 is provided between the insulator 80 and the capacitor 78 to provide a pathway for helium atoms during a leak detection test. The main difference between the present invention and the prior art is that the breathable electromechanical connection material 76 and the breathable washer 82 each include porous fillers or membranes, as described above, that create a high bulk permeability such that the leak detection gas, typically helium atoms, can readily pass through. The breathable washer 82 is either bonded to or firmly pressed against the bottom of the capacitor 78 and the top of the hermetic seal insulator 80 such that there is no gap formed that could trap contaminants or lead to high voltage field enhancement.

It will be appreciated that the passageways through the breathable electromechanical connections 76 and the breathable washer 82 are generally too small to allow water, sodium bicarbonate, solids or other contaminants to pass to the interior of the assembly 74. The passageways create a relatively high bulk permeability of the breathable electromechanical connection material 76 and breathable washer material 82 to leak detection gasses, such as helium. Such breathable materials 76 and/or 82 can be used in any type of feedthrough terminal assembly to permit passage of helium atoms under pressure during a leak detection test.

Referring back to FIG. 9, breathable electromechanical connection material 76a may also be used to connect the lead wire 83 to the first set of electrode plates in the capacitor 78. In this manner, helium atoms may permeate through additional seals to provide great opportunity for detecting leaks.

Figure 11:
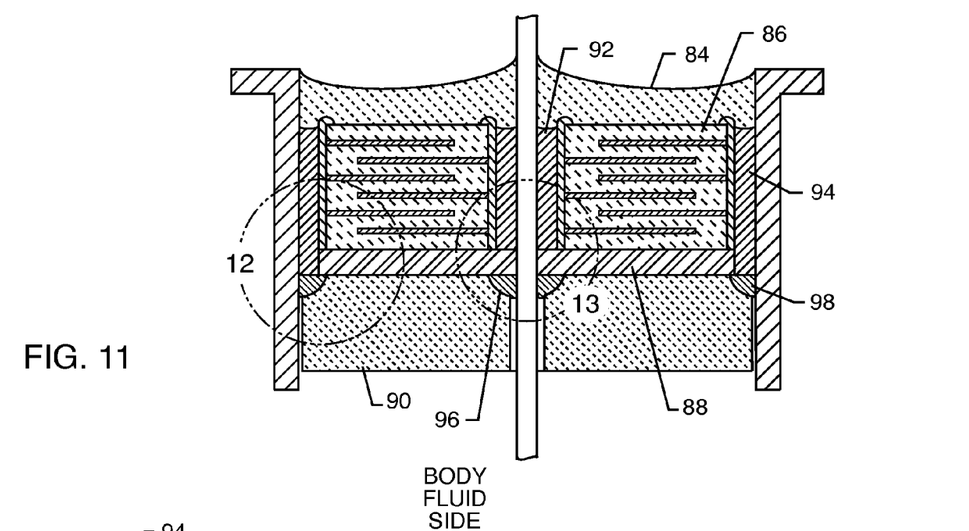
FIG. 11 is a cross-sectional view similar to FIG. 9, illustrating another unipolar terminal assembly embodying the present invention.
Figures 12, 13:
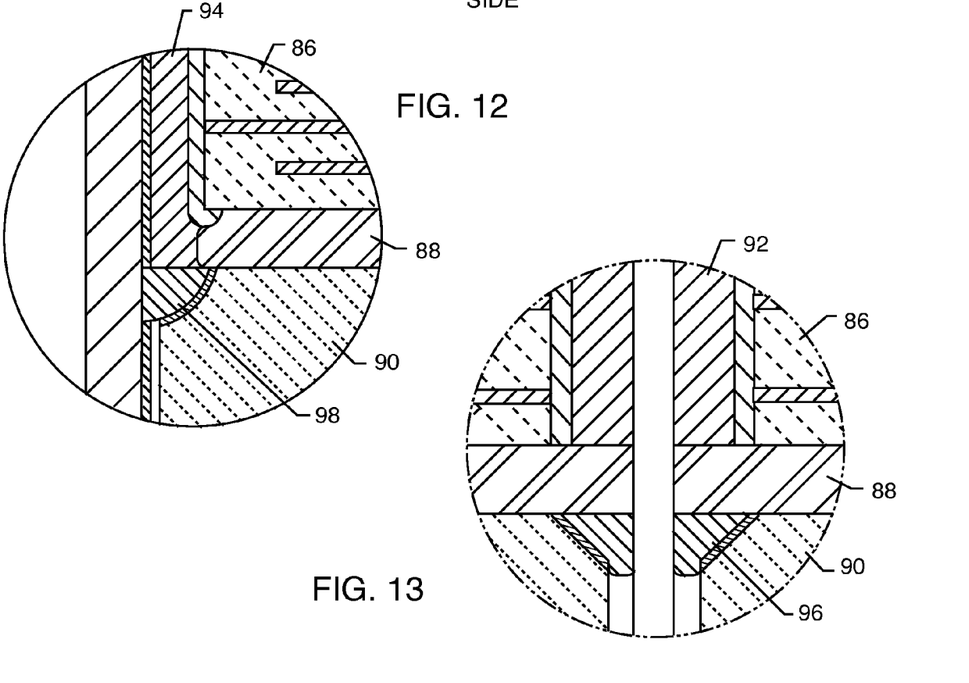
FIG. 12 is an enlarged view taken of the area indicated by the number 12 in FIG. 11.
FIG. 13 is an enlarged view taken of the area indicated by the number 13 in FIG. 12.

FIGS. 11, 12 and 13 are similar to FIGS. 28, 29 and 30 of U.S. Pat. No. 6,765,779 (the contents of which are incorporated herein), and illustrate another embodiment of the present invention. This embodiment includes a protective and cosmetic non-conductive breathable coating or breathable conformal coating 84 in accordance with the present invention dispensed over the top of the capacitor 86. A non-conductive breathable washer 88 in accordance with the present invention is placed or dispensed onto the insulator 90 into which the capacitor 86 is seated into place. Both the top and bottom surfaces of the breathable washer 88 laminate both to the bottom of the ceramic capacitor 86 and to the top of the hermetic insulator 90 during curing. In accordance with the present invention, this breathable washer 88 has sufficient permeability to readily allow helium atoms to pass during a helium leak detection test. Breathable electromechanical connection materials 92 and 94 also permit helium atoms to permeate through the materials 92 and 94 during a leak detection test. One can see that if either gold braze hermetic connection 96 or 98 is defective, then helium atoms will readily pass through the breathable materials 88, 92 and/or 94 and through the breathable coating or conformal coating 84, wherein they would be readily detected and the device would fail the leak test.

A significant advantage of this is that the gaps around the perimeters of the capacitors 40 and 68 in the connection material 46 and 72 previously described above in connection with FIGS. 3 through 7 has been eliminated in the preferred embodiments. By providing breathable conductive electromechanical connection materials 76, 92 and/or 94, or breathable non-conductive washer materials 82, 84, 88, (FIGS. 8-13), water has been generally precluded from entering the space between the breathable washer 82, 88 and the insulator 80, 90; however, helium is free to flow. This is also very important during water cleaning after sodium bicarbonate blasting. Additionally, since water molecules do not readily penetrate the porous fillers of the breathable electromechanical connection materials, this also means that the sodium bicarbonate, salts, or other solids which may be contained in the water, will not pass through.

Referring to the electrically conductive breathable connection materials such as those illustrated in FIG. 11 as materials 92 and 94, they can be made breathable by any of the aforementioned techniques of making the membranes breathable. They can also be made breathable by the addition of carbon monofilaments or carbon fibers that are porous in nature. Carbon is both conductive but can be made porous to allow helium to readily pass.

The geometries and shapes of the unipolar assemblies, as illustrated in FIGS. 8-13, can be extended to a variety of geometries and shapes including quadpolar, dual inline octapolar, inline nine polar and the like. In other words, the principles described herein can literally be applied to any feedthrough capacitor terminal assembly for human implant.

Figure 14:
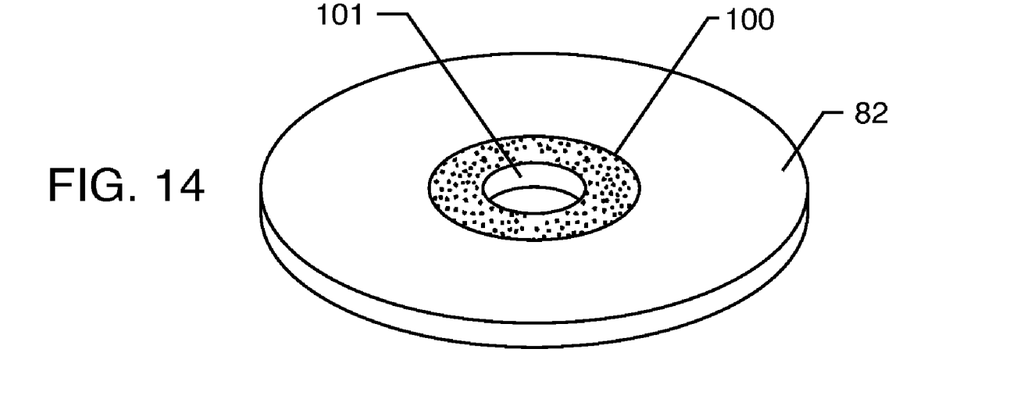
FIG. 14 is a perspective view of upper surface of the breathable washer shown in FIGS. 9 and 10, illustrated with a selective area of adhesive surrounding the center hole.

FIG. 14 illustrates the breathable washer 82 of FIGS. 9 and 10, and/or the breathable washer 88 in FIGS. 11-13, which have a selective area adhesive 100. The selective area of adhesive 100 surrounds the center hole 101 through which the lead wire 83 will pass. Referring back to FIG. 9, one can see that there is a conductive electrical attachment material 76A, which can be a thermal setting conductive adhesive such as a conductive polyimide, a solder or the like. During manufacturing, this thermal setting conductive material is typically centrifuged in place which puts great force on it. In the alternative case, during soldering, there may be fluxes or solder that would tend to flow down in the gap underneath the feedthrough capacitor. It is undesirable to have electrical conductive materials 76A disposed in places where it doesn't belong (for example, underneath the capacitor where it could create short circuits). Additionally, it is relatively undesirable to adhesively coat the entire surface of the washer 82. The reason for this is the adhesive coating material 100 would tend to flow into and block some of the pores or porosity of the breathable washer itself. Accordingly, it is a feature of the present invention to selectively place adhesives 100 in such a way that they allow helium to pass but they also selectively block the flow of the electrical conductive materials 76A and keep them in their proper locations. FIG. 14 is one such embodiment where the adhesive has been selectively placed in a circumferential manner to block said flow.

Figure 15:
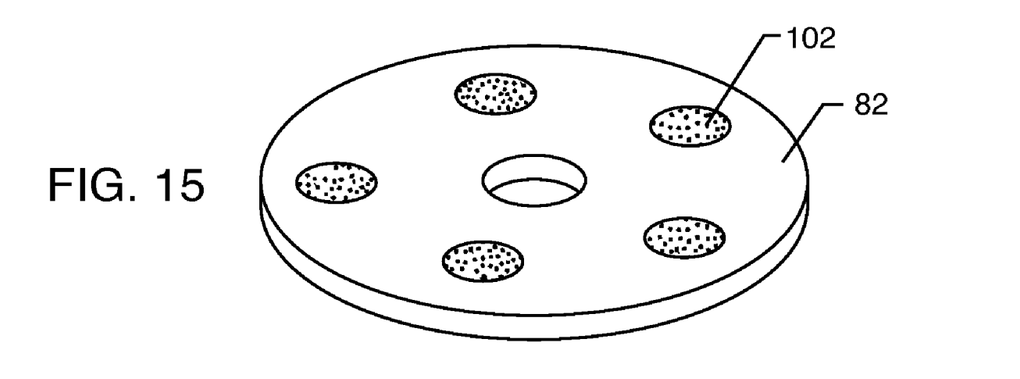
FIG. 15 is a perspective view of an opposite or bottom surface of the breathable washer shown in FIG. 14.

FIG. 15 shows the reverse side of the washer depicted in FIG. 14, illustrating the placement of selective adhesive dots 102. These, of course, can be of any shape and any location. The purpose of these dots 102 is to mechanically attach the breathable washer 82 to its substrate mounting surface, for example, the alumina ceramic insulator 80 using selectively placed dots 102, this prevents the entire surface of the breathable washer 82 from becoming sealed or saturated such that most of its pores will remain open. In other words, there are still plenty of areas where helium is free to pass.

Figure 16:
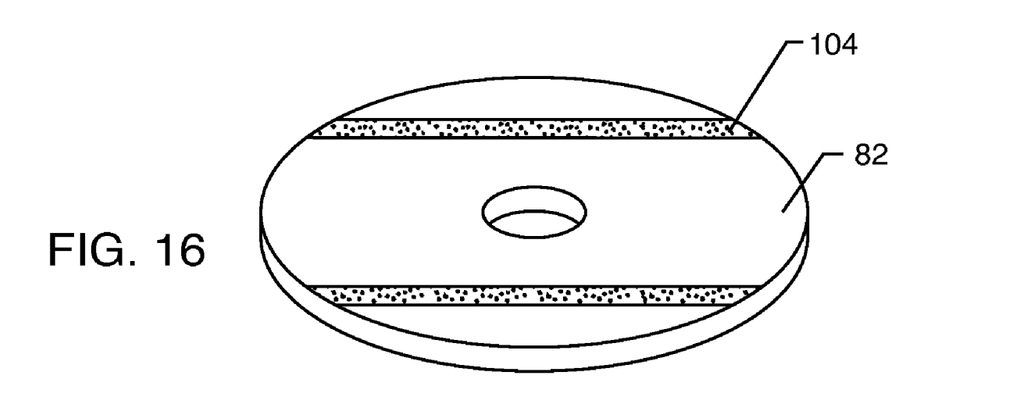
FIG. 16 is a perspective view similar to FIG. 15, illustrating an alternative configuration for applying adhesive to the bottom surface of the breathable washer.

FIG. 16 is an alternative embodiment relative to FIG. 15, showing stripes 104 instead of dots 102. It will be obvious to those skilled in the art that these stripes 104 could be squiggles or any other patterns that could be made with adhesive attachments.

Figure 17:
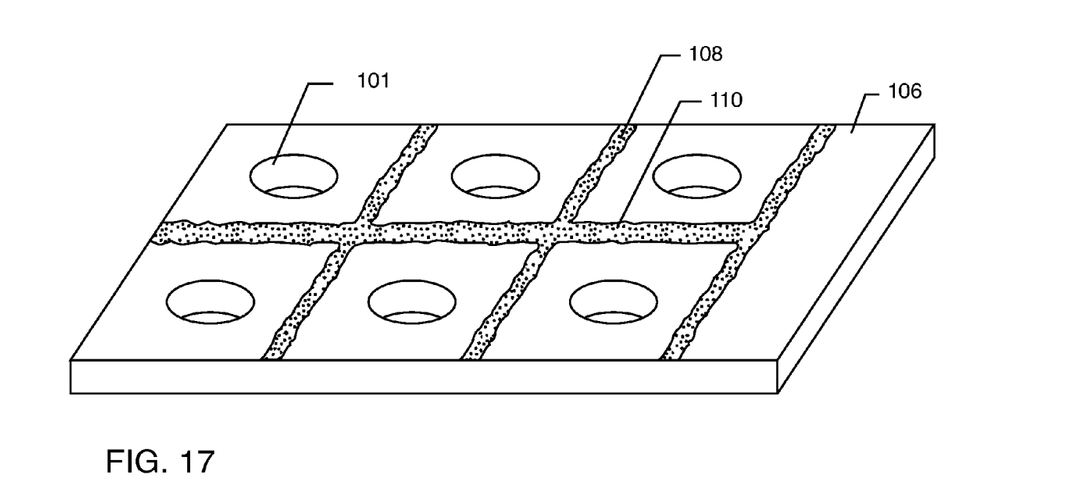
FIG. 17 is a top perspective view of a breathable washer adapted for use with a hexpolar feedthrough capacitor application.

FIG. 17 is an adaptation of a breathable washer 106 to a multi-polar feedthrough capacitor. Multi-polar feedthrough capacitors are well known in the art and include bipolar, quadpolar, hexipolar and like configurations. In FIG. 17, squiggle patters of adhesive material 108 have been placed in such a way so that there is a laminated barrier between the adjacent apertures 101. This is very important in high voltage implantable defibrillator applications in order to prevent high voltage flashover between adjacent high voltage pins.

Figure 18:
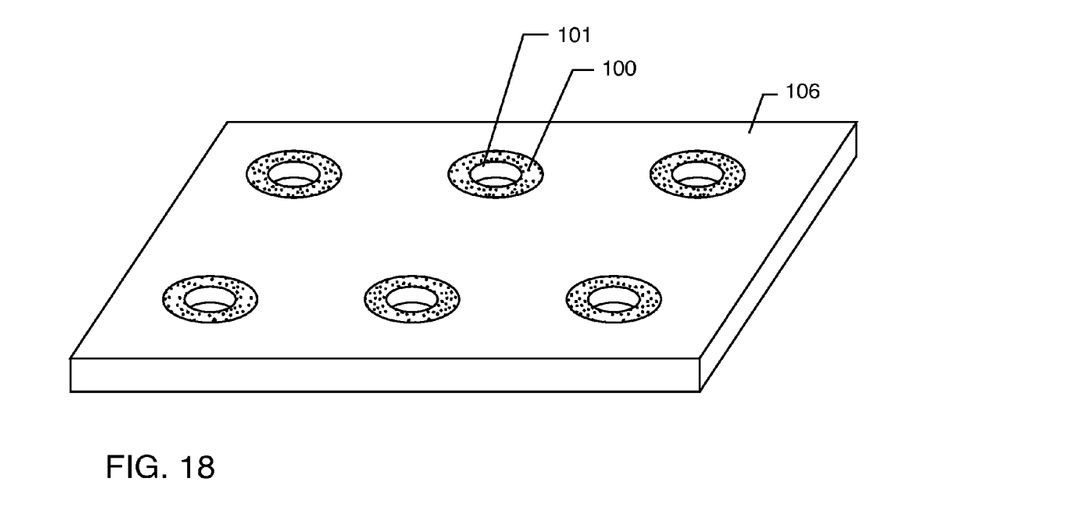
FIG. 18 is a bottom perspective view of the breathable washer shown in FIG. 17.

FIG. 18 shows the reverse side of the washer 106 of FIG. 17. This washer is designed to be laminated and sandwiched between the feedthrough capacitor and its mounting surface which is typically the alumina ceramic insulator. One can see that there is a series of circumferential areas of adhesive 100 which would be laminated against the bottom of the feedthrough capacitor. This would have the same purpose as previously described in connection with FIG. 14, thereby preventing the flow of electrical conductive materials 76A to areas where it is not desired.

In summary, adhesives can be selectively distributed as to simulate porosity enabling the filter to washer attachment to be made without compromising permeability and leak testability of the surrounding breathable medium.

Although several embodiments of the invention have been described in detail for purposes of illustration, various modifications of each may be made without departing from the spirit and scope of the invention. Accordingly, the invention is not limited, except by the appended claims.

What is claimed is:

1. A feedthrough terminal assembly for an active implantable medical device (AIMD), comprising:
   a conductive terminal pin or lead wire extending through a conductive ground plane of the AIMD in non-conductive relation;
   a feedthrough capacitor associated with the conductive terminal pin or lead wire, the capacitor having first and second sets of electrode plates;
   a hermetic insulator disposed adjacent to a face of the capacitor and disposed between the terminal pin or lead wire and the conductive ground plane;
   a breathable washer disposed between facing surfaces of the hermetic insulator and the feedthrough capacitor, the breathable washer comprising a breathable material which allows a leak detection gas to pass therethrough during a standard pressurized or vacuum pull leak detection test and yet excludes movement of liquids, dissolved solids or solid contaminants therethrough;
   means for conductively coupling the first set of electrode plates to the terminal pin or lead wire; and
   means for conductively coupling the second set of electrode plates to the ground plane.

2. The assembly of claim 1, wherein the washer includes an adhesive layer.

3. The assembly of claim 2, wherein the adhesive layer comprises a breathable material which allows leak detection gas to pass therethrough during a standard pressurized or vacuum pull leak detection test.

4. The assembly of claim 2, wherein the adhesive layer comprises a non-breathable material selectively applied to only a portion of a surface of the washer.

5. The assembly of claim 1, including a breathable coating or breathable conformal coating disposed over the capacitor on a surface disposed toward the inside of the AIMD, wherein the breathable coating or breathable conformal coating comprises a breathable material which allows leak detection gas to pass therethrough during a standard pressurized or vacuum pull leak detection test.

6. The assembly of claim 1, wherein the ground plane comprises a ferrule or a housing for the AIMD.

7. The assembly of claim 1, wherein at least one of the conductive coupling means comprises a breathable electromechanical connection material which allows leak detection gas to pass therethrough during a standard pressurized or vacuum pull leak detection test.

8. The assembly of claim 1, wherein the leak detection gas comprises helium gas.

9. The assembly of claim 1, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a nerve stimulator, a bone growth stimulator, a gastric pacemaker, or a prosthetic device.

10. A feedthrough terminal assembly for an active implantable medical device (AIMD), comprising:
    a conductive terminal pin or lead wire extending through a conductive ground plane of the AIMD in non-conductive relation;
    a feedthrough capacitor associated with the conductive terminal pin or lead wire, having first and second sets of electrode plates;
    means for conductively coupling the first set of electrode plates to the terminal pin or lead wire; and
    means for conductively coupling the second set of electrode plates to the ground plane;
    wherein at least one of the conductive coupling means comprises a breathable electromechanical connection material which allows a leak detection gas to pass therethrough during a standard pressurized or vacuum pull leak detection test and yet excludes movement of liquids, dissolved solids or solid contaminants therethrough.

11. The assembly of claim 10, including a coating or conformal coating disposed over the capacitor on a surface disposed toward and inside of the AIMD.

12. The assembly of claim 11, wherein the coating or conformal coating comprises a breathable material which allows a leak detection gas to pass therethrough during a standard pressurized or vacuum pull leak detection test.

13. The assembly of claim 10, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a nerve stimulator, a bone growth stimulator, a gastric pacemaker, or a prosthetic device.

14. The assembly of claim 13, including a hermetic insulator adjacent to a face of the capacitor and disposed between the terminal pin or lead wire and the conductive ground plane.

15. The assembly of claim 14, including a washer disposed between the hermetic insulator and the capacitor.

16. The assembly of claim 15, wherein the washer comprises a breathable washer which allows a leak detection gas to pass therethrough during a standard pressurized or vacuum pull leak detection test and yet excludes movement of liquids, dissolved solids or solid contaminants therethrough.

17. The assembly of claim 16, wherein the washer includes an adhesive layer.

18. The assembly of claim 17, wherein the adhesive layer comprises a breathable material which allows a leak detection gas to pass therethrough during a standard pressurized or vacuum pull leak detection test.

19. The assembly of claim 17, wherein the adhesive layer comprises a non-breathable material selectively applied to only a portion of a surface of the washer.

20. The assembly of claim 10, wherein the ground plane comprises a ferrule or a housing for the AIMD.

21. The assembly of claim 11, wherein the leak detection gas comprises helium gas.

22. A process for assembling a feedthrough terminal assembly for an active implantable medical device (AIMD), comprising the steps of:
    providing a feedthrough capacitor having first and second sets of electrode plates;
    conductively coupling the first set of electrode plates to a conductive terminal pin or lead wire extending through the feedthrough capacitor;
    conductively coupling the second set of electrode plates to a ground plane for the AIMD; and
    during at least one of the coupling steps, electromechanically joining the associated components with a breathable material which allows leak detection gas to pass through said coupling during a standard pressurized or vacuum pull leak detection test while simultaneously excluding movement of liquids, dissolved solids or solid contaminants therethrough.

23. The process of claim 22, including the step of providing a washer of breathable material adjacent to a surface of the capacitor.

24. The process of claim 23, wherein the washer is disposed between the capacitor and a hermetic insulator.

25. The process of claim 22, including the step of coating or conformally coating a surface of the capacitor with a breathable material.

26. The process of claim 22, including the step of treating the breathable material to create sufficient permeability to allow the leak detection gas to pass therethrough while excluding movement of liquids, dissolved solids or solid contaminants therethrough.

27. The process of claim 26, wherein the treating step includes the steps of polymerization-induced phase separation of a thermoplastic at a moderate temperature, followed by a high temperature treatment to cause oxidative thermal degradation of the thermoplastic.

28. The process of claim 27, wherein the breathable material comprises an epoxy-amine cross-linked matrix having a diamine monomer and a polyvinyl, polymethyl, and/or polyether additive.

29. The process of claim 26, wherein the treating step includes the steps of selectively removing the hyperbranched polymer phase of a cured epoxy/hyperbranched polymer blend using a solvent.

30. The process of claim 26, wherein the treating process includes the steps of adding porous fillers to the breathable material.

31. The process of claim 30, wherein the porous fillers are selected from the group consisting of porous carbon spheres, carbon nanotubes, open cell microspheres, microtublets, talc, porous filaments, carbon nanofoams, and porous fibers.

32. The process of claim 26, wherein the treating step comprises the steps of:
incorporating into a molten thermoplastic a surfactant in a sufficient gas-stabilizing amount;
pressurizing the dispersion to form a hot solution of the gas in the molten thermoplastic;
dispensing the hot solution under lower pressure, whereby the gas is released from the solution to form a hot foamed material; and
compressing the hot foam between two substrates to force the gas from the foam.

33. The process of claim 23, wherein the washer comprises a compressible gas permeable gasket or membrane.

34. The process of claim 23, wherein the washer comprises a fiber washer, a double corrugated washer, a perforated washer, or a post casting stretched membrane washer.

35. The process of claim 23, including the step of applying an adhesive layer to a surface of the washer, the adhesive layer comprising a breathable material which allows a leak detection gas to pass therethrough during a standard pressurized or vacuum pull leak detection test.

36. The process of claim 23, including the step of selectively applying a non-breathable adhesive to only a portion of a surface of the washer.

37. A process for assembling a feedthrough terminal assembly for an active implantable medical device (AIMD), comprising the steps of:
providing a feedthrough capacitor having first and second sets of electrode plates;
conductively coupling the first set of electrode plates to a conductive terminal pin or lead wire extending through the feedthrough capacitor;
conductively coupling the second set of electrode plates to a ground plane for the AIMD; and
positioning a washer adjacent to a surface of the capacitor, the washer comprising a breathable material which allows leak detection gas to pass through said washer during a standard pressurized or vacuum pull leak detection test while simultaneously excluding movement of liquids, dissolved solids or solid contaminants therethrough.

38. The process of claim 37, including the step of positioning the washer between the capacitor and a hermetic insulator.

39. The process of claim 37, including the step of coating or conformally coating a surface of the capacitor with a breathable material.

40. The process of claim 37, including the step of electromechanically joining the associated components with a breathable material which allows leak detection gas to pass through said coupling during a standard pressurized or vacuum pull leak detection test, during at least one of the coupling steps.

41. The process of claim 37, including the step of treating the breathable material to create sufficient permeability to allow the leak detection gas to pass therethrough while excluding movement of liquids, dissolved solids or solid contaminants therethrough.

42. The process of claim 41, wherein the treating step includes the steps of polymerization-induced phase separation of a thermoplastic at a moderate temperature, followed by a high temperature treatment to cause oxidative thermal degradation of the thermoplastic.

43. The process of claim 42, wherein the breathable material comprises an epoxy-amine cross-linked matrix having a diamine monomer and a polyvinyl, polymethyl, and/or polyether additive.

44. The process of claim 41, wherein the treating step includes the steps of selectively removing the hyperbranched polymer phase of a cured epoxy/hyperbranched polymer blend using a solvent.

45. The process of claim 41, wherein the treating process includes the steps of adding porous fillers to the breathable material.

46. The process of claim 45, wherein the porous fillers are selected from the group consisting of porous insulative spheres, insulative nanotubes, open cell microspheres, microtublets, talc, porous filaments, nanofoams, and porous fibers.

47. The process of claim 41, wherein the treating step comprises the steps of:
incorporating into a molten thermoplastic a surfactant in a sufficient gas-stabilizing amount;
pressurizing the dispersion to form a hot solution of the gas in the molten thermoplastic;
dispensing the hot solution under lower pressure, whereby the gas is released from the solution to form a hot foamed material; and
compressing the hot foam between two substrates to force the gas from the foam.

48. The process of claim 37, wherein the washer comprises a compressible gas permeable gasket or membrane.

49. The process of claim 37, wherein the washer comprises a fiber washer, a double corrugated washer, a perforated washer, or a post casting stretched membrane washer.

50. The process of claim 37, including the step of applying an adhesive layer to a surface of the washer, the adhesive layer comprising a breathable material which allows a leak detection gas to pass therethrough during a standard pressurized or vacuum pull leak detection test.

51. The process of claim 37, including the step of selectively applying a non-breathable adhesive to only a portion of a surface of the washer.

* * * * *